United States Patent [19]

Sih

[11] 4,271,077

[45] Jun. 2, 1981

[54] 19-HYDROXY-19-METHYL-6-HYDROXY-7A-HOMO-PGI₁ COMPOUNDS

[75] Inventor: John C. Sih, Portage, Mich.

[73] Assignee: The Upjohn Company, Kalamazoo, Mich.

[21] Appl. No.: 126,510

[22] Filed: Mar. 3, 1980

Related U.S. Application Data

[62] Division of Ser. No. 54,720, Jul. 5, 1979, Pat. No. 4,225,507.

[51] Int. Cl.³ .......................................... C07D 311/02
[52] U.S. Cl. ................................ 260/345.2; 542/416; 542/421; 542/422; 542/426; 542/431; 548/252; 548/253

[58] Field of Search ..................... 260/345.2; 542/416, 542/421, 422, 426, 431; 548/252, 253

[56] References Cited

U.S. PATENT DOCUMENTS 4,123,441  10/1978  Johnson ........................... 260/345.2

Primary Examiner—Nicky Chan
Attorney, Agent, or Firm—Robert A. Armitage

[57] ABSTRACT

The present invention provides novel 19-hydroxy-19-methyl-6-hydroxy-7a-homo-PGI₁ compounds which are useful for pharmacological purposes, e.g., anti-asthmatic indications.

2 Claims, No Drawings

19-HYDROXY-19-METHYL-6-HYDROXY-7A-HOMO-PGI$_1$ COMPOUNDS

CROSS REFERENCE TO RELATED APPLICATION

The present invention is a divisional application of U.S. Ser. No. 054,720, filed July 5, 1979, now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-19-methyl-6-hydroxy-7a-homo-PGI$_1$ compounds. The novel prostacyclin analogs are useful for pharmacological purposes, e.g., as anti-asthmatic agents. The preparation and use of these compounds is incorporated here by reference from U.S. Pat. No. 4,225,507.

PRIOR ART

For background on prostacyclin, see for example R. A. Johnson, et al., Prostaglandins 12, 915–928 (1976) and R. A. Johnson, et. al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

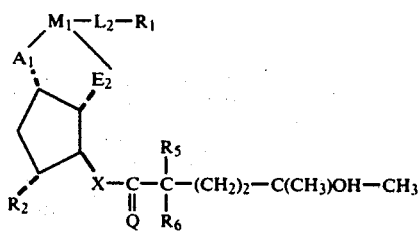

wherein A$_1$ is —O— (oxa) and E$_2$ is —CH$_2$CH$_2$—; wherein L$_2$ is
(1) —(CH$_2$)$_j$—, wherein j is one to 4, inclusive,
(2) —(CH$_2$)$_q$—CF$_2$—, wherein q is one, 2, or 3; or
(3) —CH=CH—;
wherein M$_1$ is

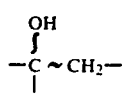

wherein Q is oxo, α-H:β-H, α-OH:β-R$_4$, or α-R$_4$:β-OH, wherein R$_4$ is hydrogen or alkyl of one to 4 carbon atoms, inclusive, wherein R$_1$ is
(1) —COOR$_3$,
(2) —CH$_2$OH,
(3) —CH$_2$N(R$_7$)(R$_8$),
(4) —CO—N(R$_7$)(R$_8$),
(5) —CO—NH—SO$_2$—R$_{15}$, or
(6) tetrazolyl,
wherein R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(Ph)—CO—CH$_3$,
(h) —(p-Ph)—NH—CO—(p-Ph)—NH—CO—CH$_3$,
(i) —(p-Ph)—NH—CO—(p-Ph),
(j) —(p-Ph)—NH—CO—CH$_3$,
(k) —(p-Ph)—NH—CO—NH$_2$,
(l) —(p-Ph)—CH=N—NH—CO—NH$_2$,
(m) β-naphthyl,
(n) —CH$_2$—CO—R$_{16}$,
wherein —(Ph)— is inter-phenylene and —(p-Ph) is inter-para-phenylene or para-phenyl;
wherein R$_{16}$ is phenyl, p-bromophenyl, p-biphenylyl, p-nitrophenyl, p-benzamidophenyl, or 2-naphthyl, or
(o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of 2 to 4 carbon atoms, inclusive,
wherein R$_2$ is hydrogen, hydroxyl, or hydroxymethyl,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and wherein X is
(1) trans—CH=CH—,
(2) cis—CH=CH—,
(3) —C≡C—, or
(4) —CH$_2$CH$_2$—.

I claim:
1. A prostacyclin-type compound of the formula

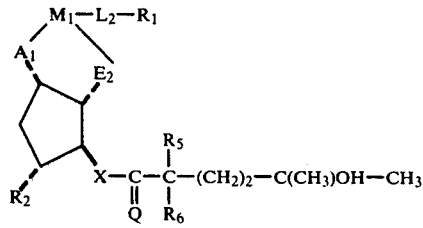

wherein A$_1$ is —O— (oxa) and E$_2$ is —CH$_2$CH$_2$—; wherein L$_2$ is
(1) —(CH$_2$)$_j$—, wherein j is one to 4, inclusive,
(2) —(CH$_2$)$_q$—CF$_2$—, wherein q is one, 2, or 3; or
(3) —CH=CH—;
wherein M$_1$ is

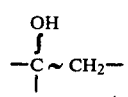

wherein Q is oxo, α-H:β-H, α-OH:β-R₄, or α-R₄:β-OH,
wherein R₄ is hydrogen or alkyl of one to 4 carbon atoms, inclusive,
wherein R₁ is
  (1) —COOR₃,
  (2) —CH₂OH,
  (3) —CH₂N(R₇)(R₈),
  (4) —CO—N(R₇)(R₈),
  (5) —CO—NH—SO₂—R₁₅, or
  (6) tetrazolyl,
wherein R₃ is
  (a) hydrogen,
  (b) alkyl of one to 12 carbon atoms, inclusive,
  (c) cycloalkyl of 3 to 10 carbon atoms, inclusive,
  (d) aralkyl of 7 to 12 carbon atoms, inclusive,
  (e) phenyl,
  (f) phenyl substituted with one, 2, or 3 chloro or alkyl groups of one to 3 carbon atoms, inclusive;
  (g) —(Ph)—CO—CH₃,
  (h) —(p-Ph)—NH—CO—(p-Ph)—NH—CO—CH₃,
  (i) —(p-Ph)—NH—CO—(p-Ph),
  (j) —(p-Ph)—NH—CO—CH₃,
  (k) —(p-Ph)—NH—CO—NH₂,
  (l) —(p-Ph)—CH=N—NH—CO—NH₂,
  (m) β-naphthyl,
  (n) —CH₂—CO—R₁₆,
wherein —(Ph)— is inter-phenylene and —(p-Ph) is inter-para-phenylene or para-phenyl;
wherein R₁₆ is phenyl, p-bromophenyl, p-bisphenylyl, p-nitrophenyl, p-benzamidophenyl, or 2-naphthyl, or
  (o) a pharmacologically acceptable cation; wherein R₇ and R₈ are hydrogen, alkyl of one to 12 carbon atoms, inclusive, benzyl, or phenyl, being the same or different, and wherein R₁₅ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of 2 to 4 carbon atoms, inclusive,
wherein R₂ is hydrogen, hydroxyl, or hydroxymethyl,
wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro, and
wherein X is
  (1) trans—CH=CH—,
  (2) cis—CH=CH—,
  (3) —C≡C—, or
  (4) —CH₂CH₂—.

2. A compound according to claim 1, wherein R₁ is —CH₂OH.

* * * * *